United States Patent
Wu et al.

(10) Patent No.: US 11,583,197 B2
(45) Date of Patent: Feb. 21, 2023

(54) METHOD AND DEVICE FOR DETECTING CARDIAC ARRHYTHMIA BASED ON PHOTOPLETHYSMOGRAPHIC SIGNAL

(71) Applicant: Acer Incorporated, New Taipei (TW)

(72) Inventors: Jo-Hua Wu, New Taipei (TW);
Hsien-Yang Chiang, New Taipei (TW);
Yu-Chun Wu, New Taipei (TW);
Pin-Cyuan Lin, New Taipei (TW);
Ke-Han Pan, New Taipei (TW);
Yueh-Yarng Tsai, New Taipei (TW)

(73) Assignee: ACER INCORPORATED, New Taipei (TW)

( * ) Notice: Subject to any disclaimer, the term of this patent is extended or adjusted under 35 U.S.C. 154(b) by 388 days.

(21) Appl. No.: 16/577,040

(22) Filed: Sep. 20, 2019

(65) Prior Publication Data

US 2020/0178821 A1    Jun. 11, 2020

(30) Foreign Application Priority Data

Dec. 5, 2018 (TW) .................................. 107143603

(51) Int. Cl.
*A61B 5/024* (2006.01)
*A61B 5/00* (2006.01)
(Continued)

(52) U.S. Cl.
CPC .......... *A61B 5/02416* (2013.01); *A61B 5/681* (2013.01); *A61B 5/7257* (2013.01);
(Continued)

(58) Field of Classification Search
CPC ... A61B 5/02416; A61B 5/681; A61B 5/7257; A61B 5/7267; A61B 5/352;
(Continued)

(56) References Cited

U.S. PATENT DOCUMENTS 9,974,487 B2    5/2018 Lin et al.
10,398,381 B1 *  9/2019 Heneghan ............ A61B 5/0022
(Continued)

FOREIGN PATENT DOCUMENTS

CN    103251405 A    8/2013
TW    201325553 A    7/2013
(Continued)

OTHER PUBLICATIONS

European Search Report dated Nov. 26, 2019, issued in application No. EP 19201198.9.
(Continued)

*Primary Examiner* — Eric F Winakur
*Assistant Examiner* — Abid A Mustansir
(74) *Attorney, Agent, or Firm* — McClure, Qualey & Rodack, LLP (57) ABSTRACT

A method for detecting cardiac arrhythmia based on a photoplethysmographic (PPG) signal is provided. The method includes: receiving a PPG signal and a motion signal corresponding to a motion made by a user; extracting PPG signal segments and motion signal segments corresponding to a time period from the PPG signal and the motion signal, respectively, at every time period; filtering out motion artifact noise in the PPG signal segments according to the PPG signal segments and the motion signal segments, and converting the PPG signal segments and the motion signal segments into PPG spectrum diagrams and motion spectrum diagrams, respectively; obtaining an estimated heart rate according to the PPG spectrum diagrams and the motion spectrum diagrams; and determining whether cardiac arrhythmia is present based on the filtered PPG signal segments and the estimated heart rate.

12 Claims, 7 Drawing Sheets

(51) Int. Cl.
    *A61B 5/0205* (2006.01)
    *A61B 5/352* (2021.01)

(52) U.S. Cl.
    CPC .......... *A61B 5/7267* (2013.01); *A61B 5/0205* (2013.01); *A61B 5/352* (2021.01); *A61B 5/725* (2013.01); *A61B 5/7207* (2013.01)

(58) Field of Classification Search
    CPC ..... A61B 5/0205; A61B 5/7207; A61B 5/725; A61B 5/7221; A61B 5/721; A61B 5/7282; A61B 5/02
    See application file for complete search history.

(56) References Cited

U.S. PATENT DOCUMENTS

| | | | |
|---|---|---|---|
| 2005/0058456 A1 | 3/2005 | Yoo | |
| 2015/0112606 A1* | 4/2015 | He | A61B 5/4809 702/19 |
| 2016/0089086 A1 | 3/2016 | Lin et al. | |
| 2016/0361021 A1* | 12/2016 | Salehizadeh | A61B 5/7253 |
| 2016/0367198 A1* | 12/2016 | Chon | A61B 5/02416 |
| 2017/0071482 A1 | 3/2017 | Chang et al. | |
| 2017/0347899 A1 | 12/2017 | Bhushan et al. | |
| 2018/0279891 A1 | 10/2018 | Miao et al. | |
| 2018/0338727 A1* | 11/2018 | Mukhopadhyay | A61B 5/721 |
| 2019/0133537 A1* | 5/2019 | Ghose | A61B 5/742 |

FOREIGN PATENT DOCUMENTS

| | | |
|---|---|---|
| TW | 201611777 A | 4/2016 |
| TW | 201801671 A | 1/2018 |

OTHER PUBLICATIONS

Chinese language Office Action dated Nov. 18, 2019, issued in application No. TW 107143603.
Chinese language Office Action dated Jan. 15, 2020, issued in application No. TW 107143603.
Fukushima, H., et al.; "Estimating heart-rate using wrist-type Photoplethysmography and acceleration sensor while running;" 34th Annual International Conference of the IEEE EMBS; Aug.-Sep. 2012; pp. 2901-2904.
Jiang, H.; "Motion-artifact resistant design of photoplethysmograph ring sensor for driver monitoring;" Dec. 2003; pp. 1-62.
Salehizadeh, S.M.A., et al.; "A Novel Time-varying Spectral Filtering Algorithm for Reconstruction of Motion Artifact Corrupted Heart Rate Signals During Intense Physical Activities Using a wearable photoplethysmogram sensor;" www.mdpi.com/journal/sensors; Dec. 2015; pp. 1-20.
Chen, H., et al.; "Hybrid classification engine for cardiac arrhythmia cloud service in elderly healthcare management;" 2014; pp. 128-134.
Dhinese language office action dated Jul. 5, 2019, issued in application No. TW 107143603.
Dhinese language office action dated Sep. 4, 2019, issued in application No. TW 107143603.

* cited by examiner

METHOD AND DEVICE FOR DETECTING CARDIAC ARRHYTHMIA BASED ON PHOTOPLETHYSMOGRAPHIC SIGNAL

CROSS REFERENCE TO RELATED APPLICATIONS

This application claims priority from Taiwan Patent Application No. 107143603, filed on Dec. 5, 2018, the disclosure of which is incorporated herein by reference in its entirety.

TECHNICAL FIELD

The present disclosure relates to a heart rate measurement technique, and more particularly, it relates to a method and device for detecting cardiac arrhythmia based on a photoplethysmographic (PPG) signal.

BACKGROUND

Heart rate may be measured using any of a variety of different sensors, including, for example, electrode-based sensors, such as EKG sensors, and optical sensors, such as photoplethysmographic (PPG) sensors. PPG sensors typically include a light source and a photodetector that are placed adjacent to a person's skin. The light source and photodetector are typically arranged so that light from the light source cannot reach the photodetector directly. However, when the PPG sensor is placed adjacent to a person's skin, light from the light source may diffuse into the person's flesh and then be emitted back out of the person's flesh so that the photodetector can detect it. The amount of light emitted from the person's flesh may vary as a function of the heart rate, since the amount of blood present in the flesh varies as a function of heart rate and the amount of light that is emitted from the person's flesh, in turn, varies as a function of the amount of blood present.

However, since PPG sensors are also more sensitive to motion artifact noise than are many other types of sensors, PPG sensors are more prone to problems with inaccuracy. Thus, a method and a device for detecting cardiac arrhythmia based on a PPG signal are desired to solve the aforementioned problems.

SUMMARY

The following summary is illustrative only and is not intended to be limiting in any way. That is, the following summary is provided to introduce concepts, highlights, benefits and advantages of the novel and non-obvious techniques described herein. Select, not all, implementations are described further in the detailed description below. Thus, the following summary is not intended to identify essential features of the claimed subject matter, nor is it intended for use in determining the scope of the claimed subject matter.

A method and a device for detecting cardiac arrhythmia based on a PPG signal are provided in the disclosure to solve the problems.

In an embodiment, a method for detecting cardiac arrhythmia based on a photoplethysmographic (PPG) signal is provided in the disclosure. The method comprises: receiving a PPG signal and a motion signal corresponding to a motion made by a user; extracting PPG signal segments and motion signal segments corresponding to a time period from the PPG signal and the motion signal, respectively, at every time period; filtering out motion artifact noise in the PPG signal segments according to the PPG signal segments and the motion signal segments, and converting the PPG signal segments and the motion signal segments into PPG spectrum diagrams and motion spectrum diagrams, respectively; obtaining an estimated heart rate according to the PPG spectrum diagrams and the motion spectrum diagrams; and determining whether cardiac arrhythmia is present based on the filtered PPG signal segments and the estimated heart rate.

In some embodiments, the step of determining whether cardiac arrhythmia is present based on the filtered PPG signal segments and the estimated heart rate further comprises: obtaining a peak-to-peak interval (PPI) in the filtered PPG signal segments according to the estimated heart rate; obtaining PPI parameters according to the PPI; and inputting the PPI parameters into a prediction model to determine whether cardiac arrhythmia is present.

In some embodiments, after receiving the PPG signal and the motion signal corresponding to the motion of the user, the method further comprises: determining whether a part of the PPG signal exceeding a threshold is lost in the PPG signal; determining whether the PPG signal is saturated when determining that no part of the PPG signal is lost; and performing an interpolation process on the PPG signal and the motion signal so that sampling rates of the PPG signal and the motion signal are consistent when determining that the PPG signal is not saturated.

In some embodiments, after extracting the PPG signal segments and the motion signal segments corresponding to a time period, the method further comprises: performing a smoothing process on the PPG signal segments and removing baseline drift; performing the smoothing process on the motion signal segments; and performing normalization on the PPG signal segments and the motion signal segments.

In some embodiments, the motion artifact noise in the PPG signal segments is filtered out by a principal component analysis (PCA).

In some embodiments, the PPG signal segments and the motion signal segments are respectively converted into the PPG spectrum diagrams and the motion spectrum diagrams by Fourier Transform.

In some embodiments, the step of obtaining the peak-to-peak interval (PPI) in the filtered PPG signal segments according to the estimated heart rate further comprises: obtaining a shortest distance between two peaks in each of the filtered PPG signal segments according to the estimated heart rate; and obtaining the PPI according to the shortest distance.

In some embodiments, the shortest distance $D_{min}$ is expressed as follows:

$$D_{min} = \frac{\text{Sampling rate}}{\text{Estimated heart rate}} - \alpha \times (\text{Sampling rate})$$

wherein $\alpha$ is a coefficient between 0 and 1, and the sampling rate is the sampling rate after performing the interpolation process on the PPG signal and the motion signal.

In some embodiments, the PPI parameters are a PPI standard deviation, a PPI root mean square of successive differences (RMSSD) and PPI entropy.

In some embodiments, the prediction model is a support vector machine (SVM) model.

In an embodiment, a device for detecting cardiac arrhythmia based on a photoplethysmographic (PPG) signal is provided. The device comprises one or more processors and one or more computer storage media for storing one or more computer-readable instructions. The processor is configured to drive the computer storage media to execute the following tasks: receiving a PPG signal and a motion signal corresponding to a motion made by a user; extracting PPG signal segments and motion signal segments corresponding to a time period from the PPG signal and the motion signal, respectively, at every time period; filtering out motion artifact noise in the PPG signal segments according to the PPG signal segments and the motion signal segments, and converting the PPG signal segments and the motion signal segments into PPG spectrum diagrams and motion spectrum diagrams, respectively; obtaining an estimated heart rate according to the PPG spectrum diagrams and the motion spectrum diagrams; and determining whether cardiac arrhythmia is present based on the filtered PPG signal segments and the estimated heart rate.

BRIEF DESCRIPTION OF DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It should be appreciated that the drawings are not necessarily to scale as some components may be shown out of proportion to the size in actual implementation in order to clearly illustrate the concept of the present disclosure.

DETAILED DESCRIPTION

Various aspects of the disclosure are described more fully below with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects. Furthermore, like numerals refer to like elements throughout the several views, and the articles "a" and "the" includes plural references, unless otherwise specified in the description.

It should be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion. (e.g., "between" versus "directly between", "adjacent" versus "directly adjacent", etc.).

Figure 1:
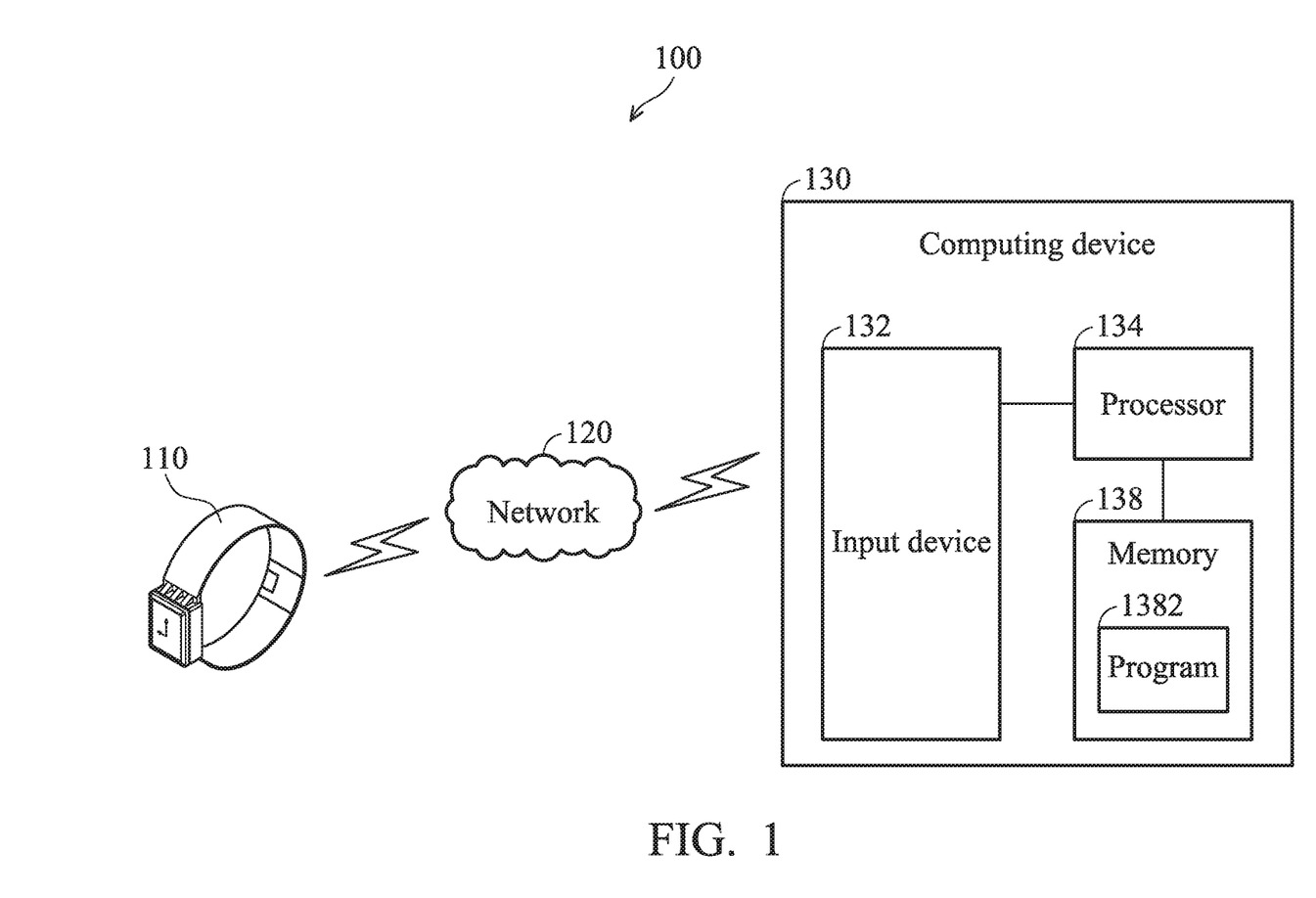
FIG. 1 shows a schematic diagram of a system for detecting cardiac arrhythmia based on a photoplethysmographic (PPG) signal according to one embodiment of the present disclosure.

FIG. 1 shows a schematic diagram of a system 100 for detecting cardiac arrhythmia based on a photoplethysmographic (PPG) signal according to one embodiment of the present disclosure. The system 100 for detecting cardiac arrhythmia based on the PPG signal may include a sensing device 110 and a computing device 130 connected to the network 120.

The sensing device 110 may be a wearable device having a photoplethysmographic (PPG) sensor and an accelerometer (ACC), for example, an Acer Leap Ware smart watch, which may be fastened to a subject (for example, the subject's head, foot, finger and wrist). The PPG sensor typically determines and estimates heart rate and respiration rate based on a PPG based heart rate method. Typically, the accelerometer is a three-dimensional (3D) or 3-axis accelerometer, wherein the accelerometer can measure acceleration in less than three dimensions. The accelerometer generates one or more motion signals indicative of acceleration. Typically, the accelerometer signals include a motion signal for each dimension of the accelerometer. The sensing device 110 may sense a motion made by a user by using the PPG sensor and the accelerometer and generate a PPG signal and a motion signal corresponding to the motion of the user. The sensing device 110 may transmit the PPG signal and the motion signal to the computing device 130 using the network 120.

The computing device 130 includes an input device 132, wherein the input device 132 is configured to receive input data from a variety of sources. For example, the computing device 130 may receive signals from the network 120 or receive the PPG signal and the motion signal transmitted by the sensing device 110. The computing device 130 is configured with a recognizer that was previously trained by other devices to recognize cardiac arrhythmia. The computing device 130 may receive the heart rate data and recognize whether cardiac arrhythmia is present in the heart rate data through the recognizer.

The computing device 130 may include a processor 134 and a memory 138 which may store program 1382. In addition, the data and the prediction model may be stored in the memory 138. In another embodiment, the computing device 130 may be used with components, systems, subsystems, and/or devices other than those that are depicted herein.

The types of computing device 130 range from small handheld devices, such as mobile telephones and handheld computers to large mainframe systems, such as mainframe computers. Examples of handheld computers include personal digital assistants (PDAs) and notebooks. The network 120 can be the Internet or optionally one of any other possible network configuration, for example, a local area network (LAN), a wide area network (WAN), Bluetooth, Wi-Fi and Wi-Fi Direct.

It should be understood that the computing device 130 shown in FIG. 1 is an example of one suitable system 100 architecture detecting cardiac arrhythmia based on the PPG signal. Each of the components shown in FIG. 1 may be implemented via any type of computing device, such as the computing device 600 described with reference to FIG. 6, for example.

Figure 2:
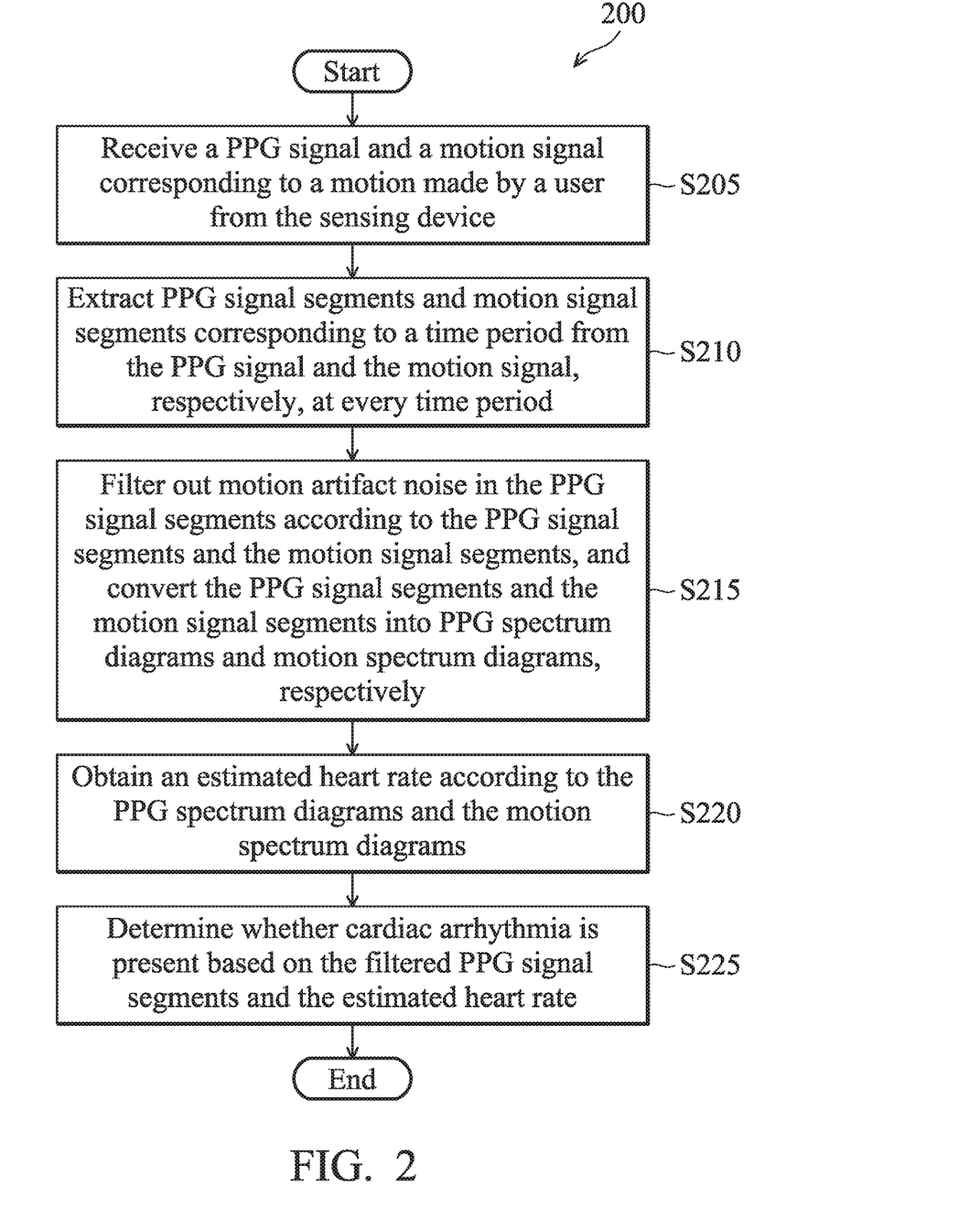
FIG. 2 is a flowchart illustrating a method for detecting cardiac arrhythmia based on a photoplethysmographic (PPG) signal according to an embodiment of the present disclosure.

FIG. 2 is a flowchart illustrating a method 200 for detecting cardiac arrhythmia based on a photoplethysmographic (PPG) signal according to an embodiment of the present disclosure. The method can be implemented in the processor 134 of the computing device 130 as shown in FIG. 1.

In step S205, the computing device receives a PPG signal and a motion signal corresponding to a motion made by a user from the sensing device. In an embodiment, the computing device further determines whether a part of the PPG signal exceeding a threshold is lost in the PPG signal after receiving the PPG signal and the motion signal corresponding to the motion of the user. The computing device determines whether the PPG signal is saturated when determining that no part of the PPG signal exceeding the threshold is lost in the PPG signal. The computing device performs an interpolation process on the PPG signal and the motion signal so that sampling rates of the PPG signal and the motion signal are consistent when determining that the PPG signal is not saturated. The computing device discards the PPG signal and the motion signal, and re-receives the PPG signal and the motion signal transmitted by the sensing device when determining that the part of the PPG signal exceeding the threshold is lost or the PPG signal is saturated.

In step S210, the computing device extracts PPG signal segments and motion signal segments corresponding to a time period from the PPG signal and the motion signal, respectively, at every time period. In an embodiment, the computing device further performs a smoothing process on the PPG signal segments and removes the baseline drift, and performs the smoothing process on the motion signal segments after extracting the PPG signal segments and the motion signal segments corresponding to the time period. Next, the computing device performs normalization on the PPG signal segments and the motion signal segments. In more detail, the normalization formula for the PPG signal segments is expressed as follows:

$$L2 - \text{Norm} = \sqrt{\vec{x}^T \vec{x}}$$

wherein $\vec{x} = [x_1, x_2, \ldots, x_{4096}]^T$ is a PPG signal segment corresponding to a time period of 8 seconds.

Figure 3A:
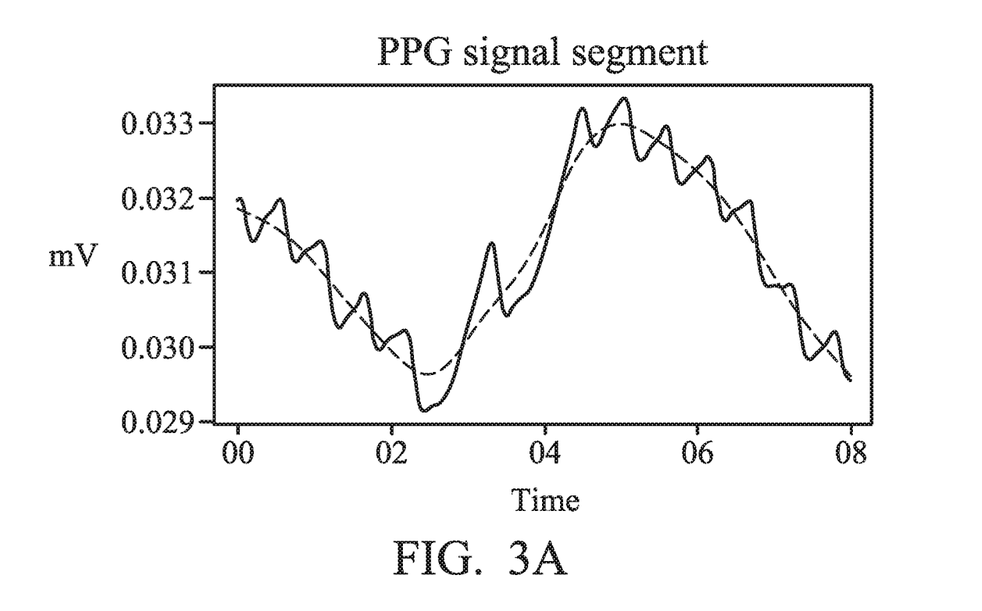
FIG. 3A to FIG. 3B are schematic diagrams for performing a smoothing process on the PPG signal segments and removing the baseline drift of the PPG signals in accordance with an embodiment of the present disclosure.
Figure 3B:
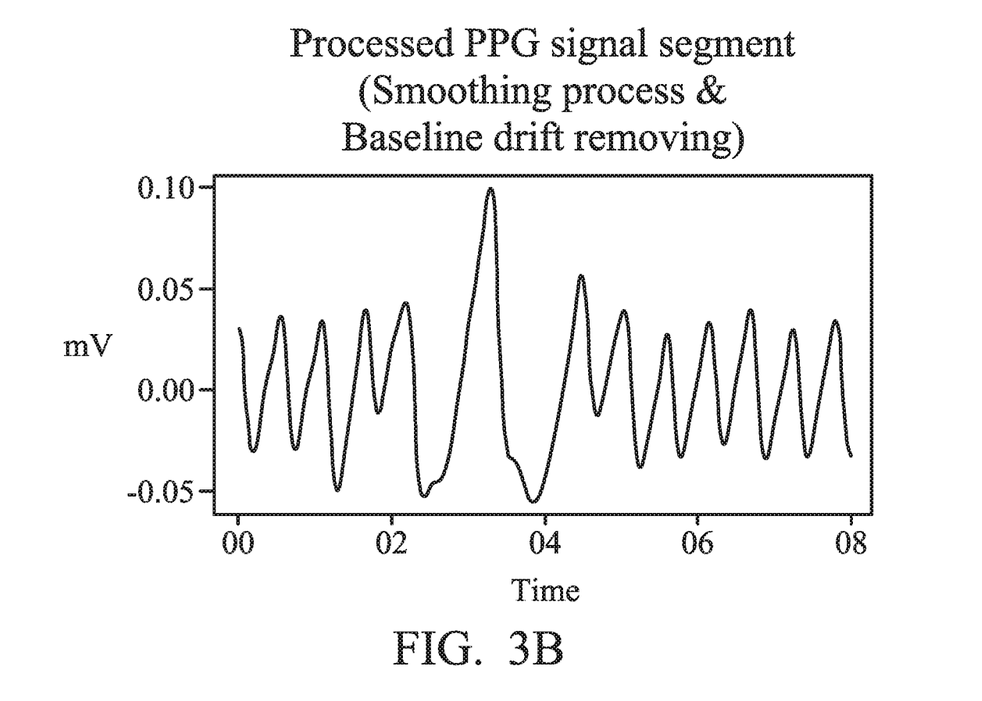

FIG. 3A to FIG. 3B are schematic diagrams for performing the smoothing process on the PPG signal segments and removing the baseline drift of the PPG signals in accordance with an embodiment of the present disclosure. As shown in FIG. 3A, the waveform of the PPG signal segment corresponding to a time period (for example, 8 seconds) obtained by the sensing device is too noisy for the time domain analysis.

The computing device may perform the smoothing process on the PPG signal segment and remove the baseline drift of the PPG signal segment. As shown in FIG. 3A, the PPG signal segment may not have a fixed baseline (shown in the dashed line). The reason causing the baseline drift may be respiratory effects, light intensity or other factors. The effects of the smoothing process on the PPG signal segment by the computing device and removing the baseline drift of the PPG signal segment is shown in FIG. 3B, so that the PPG signal segment is clearer for further analysis.

Figure 4:
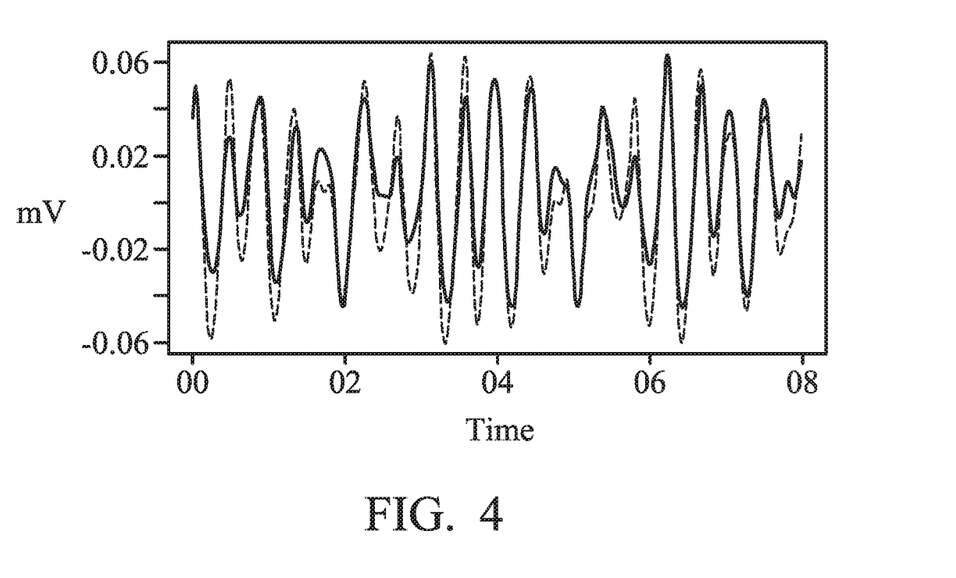
FIG. 4 is a schematic diagram of filtering out the motion artifact noise in a PPG signal segment in accordance with an embodiment of the present disclosure.

Next, in step S215, the computing device filters out motion artifact noise in the PPG signal segments according to the PPG signal segments and the motion signal segments, and converts the PPG signal segments and the motion signal segments into PPG spectrum diagrams and motion spectrum diagrams, respectively. In one embodiment, the motion artifact noise in the PPG signal segments is filtered out by a principal component analysis (PCA). FIG. 4 is a schematic diagram of filtering out the motion artifact noise in a PPG signal segment in accordance with an embodiment of the present disclosure. As shown in FIG. 4, the dashed line is the PPG signal segment that has been performed the smoothing processing and has been removed the baseline drift. The solid line is the filtered PPG signal segment after the motion artifact noise in the PPG signal segment is filtered out. In addition, in another embodiment, the PPG signal segments and the motion signal segments are respectively converted into the PPG spectrum diagrams and the motion spectrum diagrams by Fourier Transform.

Then, in step S220, the computing device obtains an estimated heart rate according to the PPG spectrum diagrams and the motion spectrum diagrams. In step S225, the computing device determines whether cardiac arrhythmia is present based on the filtered PPG signal segments and the estimated heart rate.

The following may explain in detail how the computing device obtains an estimated heart rate according to the PPG spectrum diagrams and the motion spectrum diagrams in step S220 and how the computing device determines whether cardiac arrhythmia is present based on the filtered PPG signal segments and the estimated heart rate in step S225.

Figure 5A:
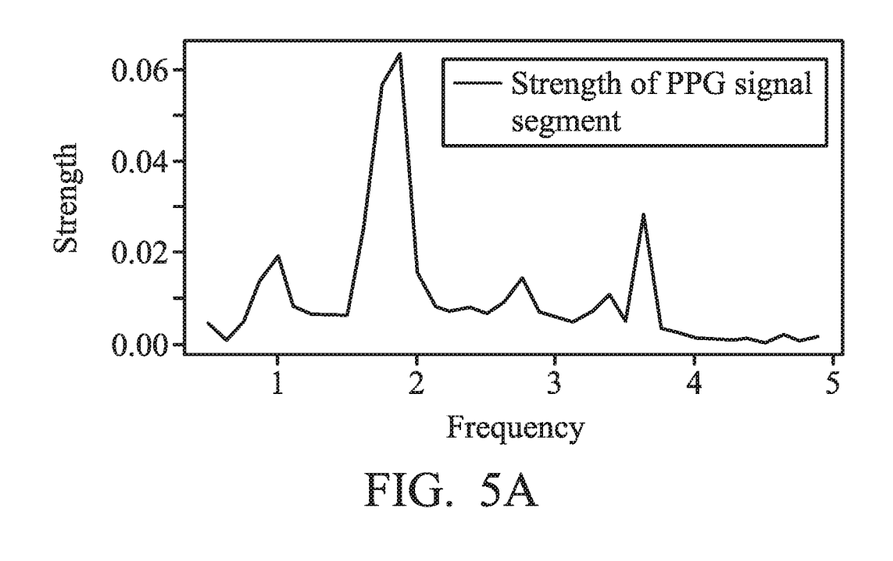
FIGS. 5A-5D are schematic diagrams of obtaining the estimated heart rate from the PPG signal segment in accordance with an embodiment of the present disclosure.
Figure 5B:
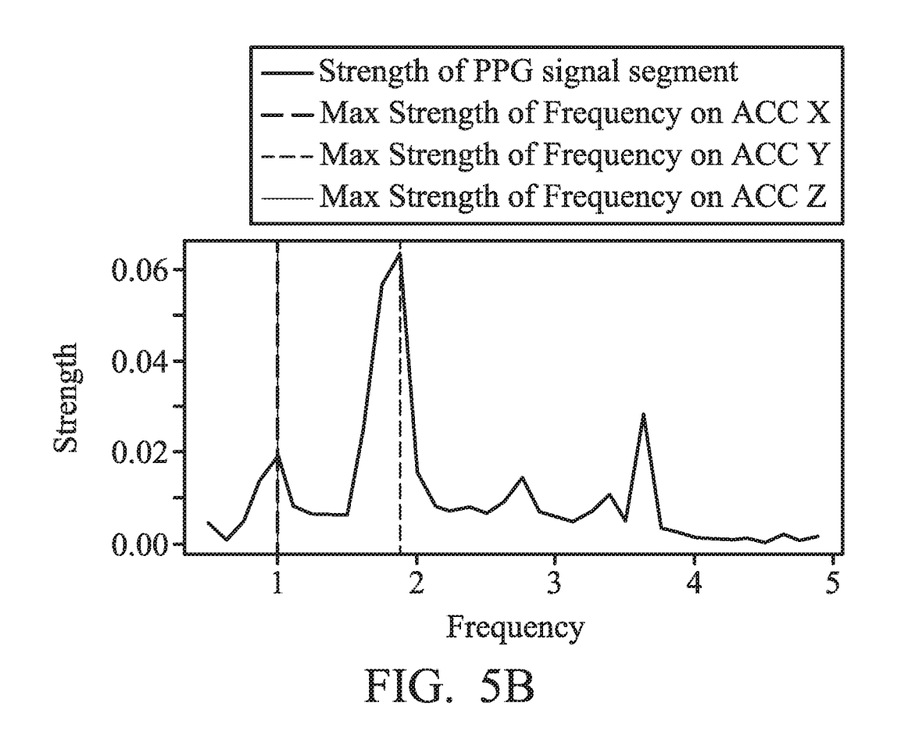
Figure 5C:
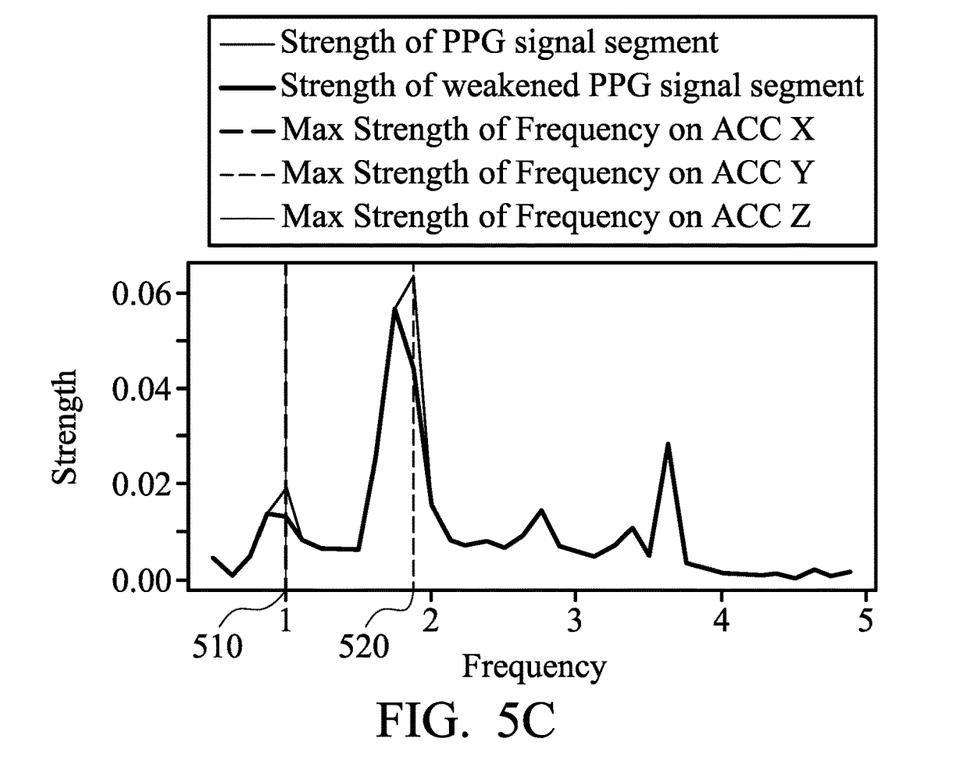
Figure 5D:
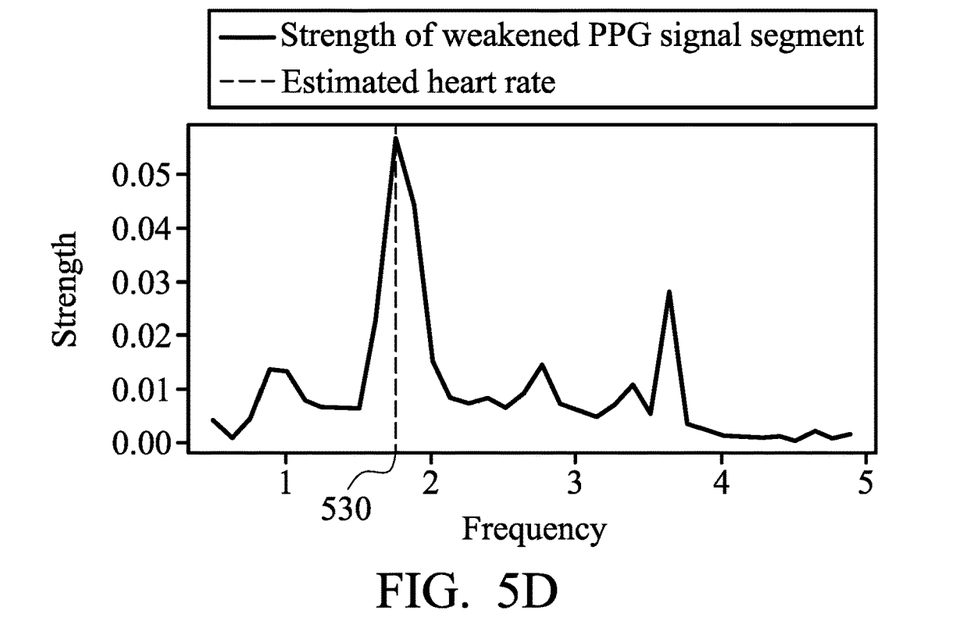

First, the computing device obtains an estimated heart rate according to each PPG spectrum diagram and the motion spectrum diagram corresponding to the PPG spectrum diagram. FIGS. 5A-5D are schematic diagrams of obtaining the estimated heart rate from the PPG signal segment in accordance with an embodiment of the present disclosure. As shown in FIG. 5A, FIG. 5A is a PPG spectrum diagram converted from a PPG signal segment. Next, the computing device finds a frequency in the motion spectrum diagram converted from the motion signal segment, wherein the frequency corresponds to the maximum strength of the ACC signal for each dimension in the frequency domain. As shown in FIG. 5B, the frequencies corresponding to the maximum strength of the ACC signal for each dimension (X-axis, Y-axis and Z-axis) are displayed in the PPG spectrum diagram converted from the PPG signal segment. In addition, the computing device may attenuate the frequency corresponding to the maximum strength of the ACC signal for each dimension to a preset multiple of the original frequency in the PPG spectrum diagram converted from the PPG signal segment to weaken the impact of the motion, wherein the preset multiple is a value between 0 and 1. In one embodiment, the value is 0.7. As shown in FIG. 5C, it is assumed that the preset multiple is 0.7. At frequencies 510 and 520 corresponding to the maximum strength of the ACC signal for each dimension, the strength of the weakened PPG signal segment (indicated by the thick line) is 0.7 times the original strength. The computing device then finds the frequency corresponding to the maximum strength in the attenuated PPG signal segment and uses this frequency as the estimated heart rate. As shown in FIG. 5D, the frequency 530 corresponding to the maximum strength is set to the estimated heart rate.

Next, the computing device obtains a peak-to-peak interval (PPI) in the filtered PPG signal segment according to the estimated heart rate. Specifically, the computing device obtains a shortest distance between two peaks in each of the filtered PPG signal segments according to the estimated heart rate, wherein the shortest distance $D_{min}$ is expressed as follows:

$$D_{min} = \frac{\text{Sampling rate}}{\text{Estimated heart rate}} - \alpha \times (\text{Sampling rate})$$

wherein $\alpha$ is a coefficient between 0 and 1, and the sampling rate is the sampling rate after performing the interpolation process on the PPG signal and the motion signal.

The computing device finds a peak position in each of the filtered PPG signal segments according to the shortest distance to ensure that the peak position found by the computing device is more reasonable. The computing device then stitches the peak locations in all of the filtered PPG signal segments sequentially to obtain all of the PPIs in all of the filtered PPG signal segments. The computing device obtains PPI parameters according to all PPIs in all filtered PPG signal segments, wherein the PPI parameters are a PPI standard deviation (SD), a PPI root mean square of successive differences (RMSSD), and PPI entropy. The formula of the PPI SD can be expressed as follows:

$$PPISD = \sqrt{\frac{1}{n-1} \sum_{i=1}^{n} (PPI_i - \overline{PPI})^2}$$

wherein n is the total number of PPIs in all filtered PPG signal segments. The formula of the PPI RMSSD can be expressed as follows:

$$PPIRMSSD = \sqrt{\frac{1}{n} \sum_{i=2}^{n} (PPI_i - PPI_{i-1})^2}$$

wherein n is the total number of PPIs in all filtered PPG signal segments. The formula of the PPI entropy can be expressed as follows:

$$PPI \text{ Entropy} = -\sum_{i=1}^{k} \widehat{p}_i \log(\widehat{p}_i)$$

wherein $\widehat{p}_i$ is a sample probability value of the i-th segment between the PPI minimum and the PPI maximum in all PPIs which is cut into k segments.

The computing device inputs the PPI parameters to a prediction model to determine whether cardiac arrhythmia is present. In an embodiment, the prediction model is a support vector machine (SVM) model. Specifically, the prediction model is a pre-trained model. When the PPI parameters are input to a prediction model, the prediction model outputs a predicted probability value corresponding to the PPI parameters. When the predicted probability value is below a first threshold, the computing device determines that there is no cardiac arrhythmia. When the predicted probability value is between the first threshold and the second threshold, the computing device determines that the PPG signal cannot be used to determine whether cardiac arrhythmia is present. When the predicted probability value is greater than the third threshold, the computing device determines that cardiac arrhythmia is present.

As described above, the method and device for detecting cardiac arrhythmia based on the photoplethysmographic (PPG) signal according to the present disclosure may restore a reasonable position of the real peak of the PPG signal under regular or irregular motion to reduce the artifact noise in the PPG signal caused by the motion. Therefore, the PPG signal processed by the method and the device of the present disclosure can filter out the influence of the motion, so as to effectively determine whether the user has abnormality of the cardiac arrhythmia and reduce the probability of delaying the treatment.

Figure 6:
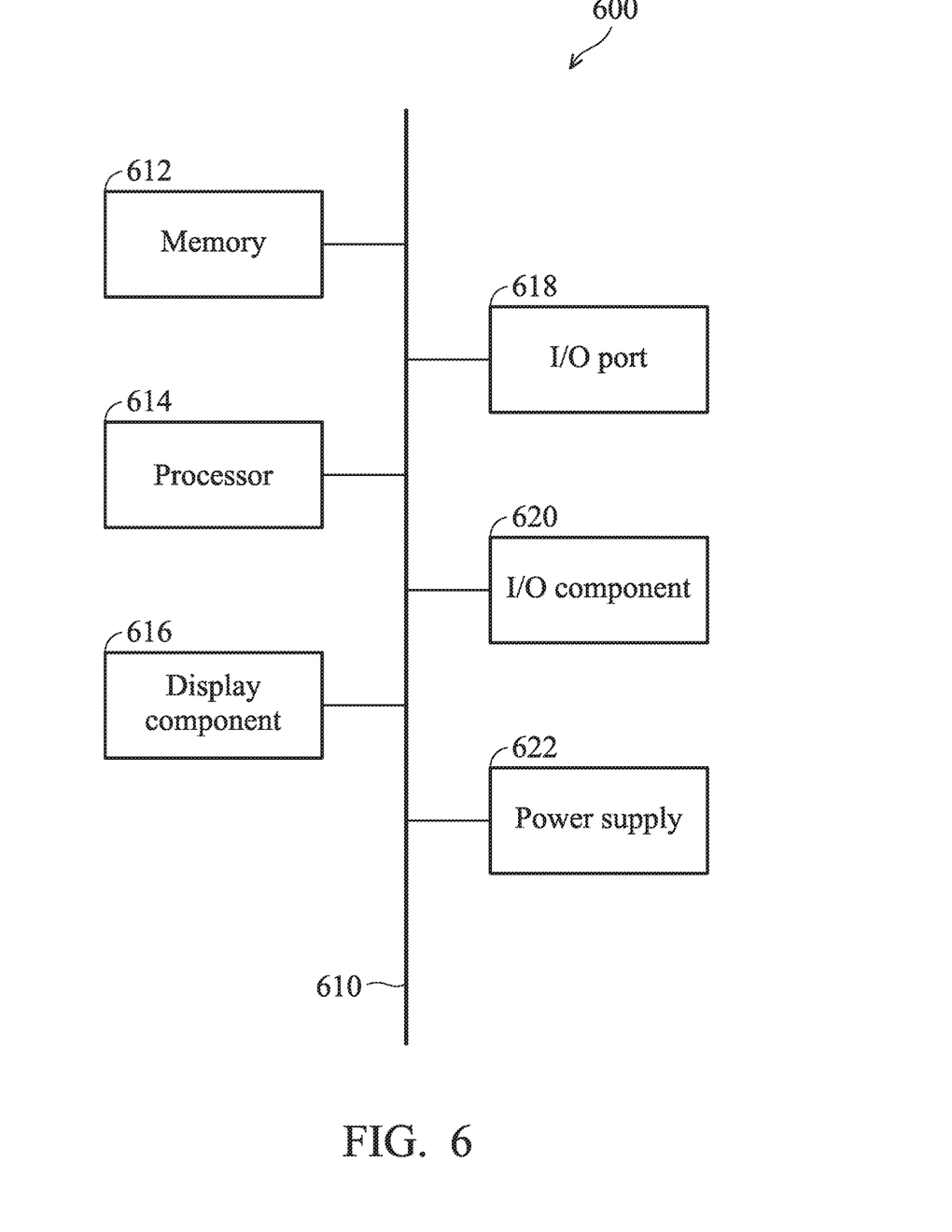
FIG. 6 illustrates an exemplary operating environment for implementing embodiments of the present disclosure.

Having described embodiments of the present disclosure, an exemplary operating environment in which embodiments of the present disclosure may be implemented is described below. Referring to FIG. 6, an exemplary operating environment for implementing embodiments of the present disclosure is shown and generally known as a computing device 600. The computing device 600 is merely an example of a suitable computing environment and is not intended to limit the scope of use or functionality of the disclosure. Neither should the computing device 600 be interpreted as having any dependency or requirement relating to any one or combination of components illustrated.

With reference to FIG. 6, the computing device 600 may include a bus 610 that is directly or indirectly coupled to the following devices: one or more memories 612, one or more processors 614, one or more display components 616, one or more input/output (I/O) ports 618, one or more input/output components 620, and an illustrative power supply 622. The bus 610 may represent one or more kinds of busses (such as an address bus, data bus, or any combination thereof). Although the various blocks of FIG. 6 are shown with lines for the sake of clarity, and in reality, the boundaries of the various components are not specific. For example, the display component such as a display device may be considered an I/O component and the processor may include a memory.

The computing device 600 typically includes a variety of computer-readable media. The computer-readable media can be any available media that can be accessed by computing device 600 and includes both volatile and nonvolatile media, removable and non-removable media. By way of example, but not limitation, computer-readable media may comprise computer storage media and communication media. The computer storage media may include volatile and nonvolatile, removable and non-removable media implemented in any method or technology for storage of information such as computer-readable instructions, data structures, program modules or other data. The computer storage media may include, but not limit to, random access memory (RAM), read-only memory (ROM), electricallyerasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by the computing device 600. The computer storage media may not comprise signal per se.

The communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, but not limitation, communication media includes wired media such as a wired network or direct-wired connection, and wireless media such as acoustic, RF, infrared and other wireless media or any combination thereof.

The memory 612 may include computer-storage media in the form of volatile and/or nonvolatile memory. The memory may be removable, non-removable, or a combination thereof. Exemplary hardware devices include solid-state memory, hard drives, optical-disc drives, etc. The computing device 600 includes one or more processors that read data from various entities such as the memory 612 or the I/O components 620. The presentation component(s) 616 present data indications to a user or other device. Exemplary presentation components include a display device, speaker, printing component, vibrating component, etc.

The I/O ports 618 allow the computing device 600 to be logically coupled to other devices including the I/O components 620, some of which may be embedded. Illustrative components include a microphone, joystick, game pad, satellite dish, scanner, printer, wireless device, etc. The I/O components 620 may provide a natural user interface (NUI) that processes gestures, voice, or other physiological inputs generated by a user. For example, inputs may be transmitted to an appropriate network element for further processing. A NUI may be implemented to realize speech recognition, touch and stylus recognition, face recognition, biometric recognition, gesture recognition both on screen and adjacent to the screen, air gestures, head and eye tracking, touch recognition associated with displays on the computing device 600, or any combination of. The computing device 600 may be equipped with depth cameras, such as stereoscopic camera systems, infrared camera systems, RGB camera systems, any combination of thereof to realize gesture detection and recognition. Furthermore, the computing device 600 may be equipped with accelerometers or gyroscopes that enable detection of motion. The output of the accelerometers or gyroscopes may be provided to the display of the computing device 600 to carry out immersive augmented reality or virtual reality.

Furthermore, the processor 614 in the computing device 600 can execute the program code in the memory 612 to perform the above-described actions and steps or other descriptions herein.

It should be understood that any specific order or hierarchy of steps in any disclosed process is an example of a sample approach. Based upon design preferences, it should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for detecting cardiac arrhythmia based on a photoplethysmographic (PPG) signal, comprising:

receiving a PPG signal and a motion signal corresponding to a motion made by a user;

extracting PPG signal segments and motion signal segments corresponding to a time period from the PPG signal and the motion signal, respectively, at every time period;

determining whether a part of the PPG signal exceeding a threshold is lost in the PPG signal;

determining whether the PPG signal is saturated when determining that no part of the PPG signal is lost; and performing an interpolation process on the PPG signal and the motion signal so that sampling rates of the PPG signal and the motion signal are consistent when determining that the PPG signal is not saturated;

filtering out motion artifact noise in the PPG signal segments according to the PPG signal segments and the motion signal segments, and converting the PPG signal segments and the motion signal segments into PPG spectrum diagrams and motion spectrum diagrams, respectively;

obtaining an estimated heart rate according to the PPG spectrum diagrams and the motion spectrum diagrams; and determining whether cardiac arrhythmia is present based on the filtered PPG signal segments and the estimated heart rate, wherein the step of determining whether cardiac arrhythmia is present based on the filtered PPG signal segments and the estimated heart rate further comprises:

obtaining a shortest distance between two peaks in each of the filtered PPG signal segments according to the estimated heart rate;

obtaining a peak-to-peak interval (PPI) according to the shortest distance; obtaining PPI parameters according to the PPI; and inputting the PPI parameters into a prediction model to determine whether cardiac arrhythmia is present, wherein the shortest distance Dmin is expressed as follows:

Dmin=(sampling rate/estimated heart rate)-α× (Sampling rate)

wherein α is a coefficient between 0 and 1, and the sampling rate is the sampling rate after performing the interpolation process on the PPG signal and the motion signal.

2. The method for detecting cardiac arrhythmia based on a photoplethysmographic (PPG) signal as claimed in claim 1, wherein after extracting the PPG signal segments and the motion signal segments corresponding to a time period, the method further comprises:
performing a smoothing process on the PPG signal segments and removing baseline drift;
performing the smoothing process on the motion signal segments; and
performing normalization on the PPG signal segments and the motion signal segments.

3. The method for detecting cardiac arrhythmia based on a photoplethysmographic (PPG) signal as claimed in claim 1, wherein the motion artifact noise in the PPG signal segments is filtered out by a principal component analysis (PCA).

4. The method for detecting cardiac arrhythmia based on a photoplethysmographic (PPG) signal as claimed in claim 1, wherein the PPG signal segments and the motion signal segments are respectively converted into the PPG spectrum diagrams and the motion spectrum diagrams by Fourier Transform.

5. The method for detecting cardiac arrhythmia based on a photoplethysmographic (PPG) signal as claimed in claim 1, wherein the PPI parameters are a PPI standard deviation, a PPI root mean square of successive differences (RMSSD) and PPI entropy.

6. The method for detecting cardiac arrhythmia based on a photoplethysmographic (PPG) signal as claimed in claim 1, wherein the prediction model is a support vector machine (SVM) model.

7. A device for detecting cardiac arrhythmia based on a photoplethysmographic (PPG) signal, comprising:
one or more processors; and
one or more computer storage media for storing one or more computer-readable instructions, wherein the processor is configured to drive the computer storage media to execute the following tasks:
receiving a PPG signal and a motion signal corresponding to a motion made by a user;
extracting PPG signal segments and motion signal segments corresponding to a time period from the PPG signal and the motion signal, respectively, at every time period;
determining whether a part of the PPG signal exceeding a threshold is lost in the PPG signal;
determining whether the PPG signal is saturated when determining that no part of the PPG signal is lost; and
performing an interpolation process on the PPG signal and the motion signal so that sampling rates of the PPG signal and the motion signal are consistent when determining that the PPG signal is not saturated;
filtering out motion artifact noise in the PPG signal segments according to the PPG signal segments and the motion signal segments, and converting the PPG signal segments and the motion signal segments into PPG spectrum diagrams and motion spectrum diagrams, respectively;
obtaining an estimated heart rate according to the PPG spectrum diagrams and the motion spectrum diagrams; and
determining whether cardiac arrhythmia is present based on the filtered PPG signal segments and the estimated heart rate,
wherein the step of determining whether cardiac arrhythmia is present based on the filtered PPG signal segments and the estimated heart rate further comprises:
obtaining a shortest distance between two peaks in each of the filtered PPG signal segments according to the estimated heart rate;
obtaining a peak-to-peak interval (PPI) according to the shortest distance; obtaining PPI parameters according to the PPI; and
inputting the PPI parameters into a prediction model to determine whether cardiac arrhythmia is present,
wherein the shortest distance Dmin is expressed as follows:
Dmin=(sampling rate/estimated heart rate)- $\alpha$x (Sampling rate)
wherein $\alpha$ is a coefficient between 0 and 1, and the sampling rate is the sampling rate after performing the interpolation process on the PPG signal and the motion signal.

8. The device for detecting cardiac arrhythmia based on a photoplethysmographic (PPG) signal as claimed in claim 7, wherein after extracting the PPG signal segments and the motion signal segments corresponding to a time period, the processor further executes the following tasks:
performing a smoothing process on the PPG signal segments and removing baseline drift;
performing the smoothing process on the motion signal segments; and
performing normalization on the PPG signal segments and the motion signal segments.

9. The device for detecting cardiac arrhythmia based on a photoplethysmographic (PPG) signal as claimed in claim 7, wherein the motion artifact noise in the PPG signal segments is filtered out by a principal component analysis (PCA).

10. The device for detecting cardiac arrhythmia based on a photoplethysmographic (PPG) signal as claimed in claim 7, wherein the PPG signal segments and the motion signal segments are respectively converted into the PPG spectrum diagrams and the motion spectrum diagrams by Fourier Transform.

11. The device for detecting cardiac arrhythmia based on a photoplethysmographic (PPG) signal as claimed in claim 7, wherein the PPI parameters are a PPI standard deviation, a PPI root mean square of successive differences (RMSSD) and PPI entropy.

12. The device for detecting cardiac arrhythmia based on a photoplethysmographic (PPG) signal as claimed in claim 7, wherein the prediction model is a support vector machine (SVM) model.

* * * * *